(12) United States Patent
Freeman

(10) Patent No.: US 7,279,300 B2
(45) Date of Patent: Oct. 9, 2007

(54) PROTOZOAN RHOMBOID PROTEINS

(75) Inventor: Matthew Freeman, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 10/533,266

(22) PCT Filed: Nov. 3, 2003

(86) PCT No.: PCT/GB03/04711

§ 371 (c)(1),
(2), (4) Date: Nov. 28, 2005

(87) PCT Pub. No.: WO2004/040009

PCT Pub. Date: May 13, 2004

(65) Prior Publication Data

US 2006/0127968 A1     Jun. 15, 2006

Related U.S. Application Data

(60) Provisional application No. 60/422,861, filed on Nov. 1, 2002.

(51) Int. Cl.
*C12Q 1/37* (2006.01)
(52) U.S. Cl. ..................................................... 435/23
(58) Field of Classification Search ..................... None
See application file for complete search history.

(56) References Cited

OTHER PUBLICATIONS

Blackman et al. JBC 1998;273(36):23398-23409.*
Urban et al. Cell 2001;107:173-182.*
Blackman et al., Secondary Processing of the *Plasmodium falciparum* Merozoite Surface Protein-1 (MSP1) by a Calcium-Dependent Membrane-Bound Serine Protease: Shedding of $MSP1_{33}$ as a Noncovalently Associated Complex with Other Fragments of the MSP1, Mol. and Biochem. Parasitology, 1992, 50: 307-315.
Blackman et al., A Conserved Parasite Serine Protease Processes the *Plasmodium falciparum* Merozoite Surface Protein-1, Mol. and Biochem. Parasitology, 1993, 62: 103-114.
Carruthers et al., The Toxoplasma Adhesive Protein MIC2 is Proteolytically Processed at Multiple Sites by Two Parasite-Derived Proteases, The J. of Biol. Chem., 2000, 275(19): 14346-14353.
Koonin et al., The Rhomboids: A Nearly Ubiquitous Family of Intramembrane Serine Proteases that Probably Evolved by Multiple Ancient Horizontal Gene Transfers, 2003, Gen. Biol., 4(3): R19.
Opitz et al., Intramembrane Cleavage of Microneme Proteins at the Surface of the Apicompiexan Parasite *Toxoplasma gondii*, EMBO Jrnl., 2002, 21(7): 1577-1585.
Urban et al., Substrate Specificity of Rhomboid Intramembrane Proteases is Governed by Helix-Breaking Residues in the Substrate Transmembrane Domain, 2003, Mole. Cell, 11: 1425-1434.
Urban et al., Intramembrane Proteolysis Controls Diverse Signalling Pathways Throughout Evolution, 2002, 512-518.
Urban et al., Conservation of Intramembrane Proteolytic Activity and Substrate Specificity in Prokaryotic and Eukaryotic Rhomboids, 2002, 12: 1507-1512.

* cited by examiner

*Primary Examiner*—Ralph Gitomer
*Assistant Examiner*—Bin Shen
(74) *Attorney, Agent, or Firm*—Bozicevic Field & Francis LLP; Pamela J. Sherwood

(57) ABSTRACT

Protozoan Rhomboid Proteins. The invention relates to the identification of protozoan Rhomboid proteins that are involved in the invasive processes of protozoan pathogens, such as *P falciparum*. Modulation of these Rhomboid proteins may this be useful in treating protozoan pathogen infection. Methods and means relating to the modulation of protozoan Rhomboid proteins are provided herein.

20 Claims, 1 Drawing Sheet

| | |
|---|---|
| EtMIC4 | ...GFPTAAVAGGVGGVLLLAAVGGGV--AAY (SEQ ID NO:3) |
| TgMIC2 | ...SGIAGAIAGGVIGGLILLGAAG---GASY (SEQ ID NO:4) |
| TgMIC6 | ...SGHAGAIAGGVIGGLLLLSAAGAG--VAY (SEQ ID NO:5) |
| TgMIC12 | ...GVPVAAIAGGVVGGVLLIAGGAGA--AVY (SEQ ID NO:6) |
| PbTRAP | ...SNNGIKIAGGIIGGLAIIGCIG----VGY (SEQ ID NO:7) |
| PfTRAP | ...SDNKYKIAGGIAGGLALLACAG----LAY (SEQ ID NO:8) |
| EtMIC1 | ...GFPTAAVAGGVAGGVLAIAAGAG---AFY (SEQ ID NO:9) |
| Sm70 | ...GMPTAAIAGGIVGGVLLLGAAGGG--AAY (SEQ ID NO:10) |
| TgAMA1 | ...GSNTALIAGLAVGGVLLLALLGG---GCY (SEQ ID NO:11) |
| DmSPITZ | ...PRPMLEKASIASGAMCALVFMLFVCLAFYL (SEQ ID NO:12) |
| DmKEREN | ...NRVMLEKASIVSGATLALLFMAMCCVVLYL (SEQ ID NO:13) | lumenal/extracellular                                  cytoplasmic

FIG. 1

PROTOZOAN RHOMBOID PROTEINS

The present invention relates to the invasive processes of protozoan pathogens and in particular to the provision of therapeutic compounds which block these processes and may thus be useful in treating protozoan pathogen infection.

Protozoan pathogens of the *Apicomplexa* family, which include the malaria parasite *P. falciparum*, express a number of membrane-tethered adhesion proteins that are essential for the recognition and binding of host (e.g. mammalian) cells. An essential step in the invasive processes by which these pathogens enter host cells is the release of these adhesion proteins from the surface of the pathogen by proteolytic cleavage. Some of these adhesion proteins are cleaved within the transmembrane domain (TMD) (Opitz et al (2002) EMBO J. 21 7 1577-1585).

The present inventors have discovered that Rhomboid polypeptides are involved in the cleavage of protozoan adhesion molecules. Rhomboid polypeptides are intra-membrane serine proteases, which are widely conserved throughout evolution and act on a range of physiological substrates. Inhibition of the protozoan Rhomboid activity reduces adhesion polypeptide cleavage and may thus reduce the invasiveness of the protozoan pathogen.

A first aspect of the invention provides a method for identifying and/or obtaining a compound that inhibits invasiveness of a protozoan pathogen, for example by inhibiting the activity of a protozoan Rhomboid polypeptide, which method comprises:

(a) bringing into contact an isolated Rhomboid polypeptide and an isolated substrate polypeptide in the presence of a test compound; and (b) determining proteolytic cleavage of the substrate polypeptide.

The Rhomboid and substrate polypeptides may be contacted out under conditions in which the Rhomboid polypeptide normally catalyses proteolytic cleavage of the substrate polypeptide.

The polypeptides may be contacted in a reaction medium in an isolated form or may be comprised in a liposome or host cell, preferably, a host cell in which the Rhomboid polypeptide and substrate are not naturally expressed. The Rhomboid polypeptide may, for example, act on a membrane-bound substrate polypeptide to generate a soluble product, which is detected.

Cleavage of the substrate polypeptide may be determined in the presence and absence of test compound. A reduction or decrease in cleavage in the presence of the test compound relative to the absence of test compound may be indicative of the test compound being an inhibitor of protozoan Rhomboid protease activity. Such a compound may inhibit adhesive micronemal polypeptide cleavage and thus protozoan pathogen infectivity.

A Rhomboid polypeptide may be a protozoan Rhomboid protein, for example a Rhomboid polypeptide from an apicomplexan pathogen. Suitable protozoan Rhomboid polypeptides include any one of Rhomboids 1-7 of *P. falciparum* as shown in Table 1a.

In some preferred embodiments, the Rhomboid polypeptide may be a non-mitochondrial Rhomboid, such as Rho1, Rho3, Rho4, Rho6 or Rho7 of *P. falciparum*, in particular Rho1, Rho3, Rho4 or Rho7.

Amino acid residues of Rhomboid and substrate polypeptides are described in the present application with reference to their position in the *Drosophila* Rhomboid-1 and Spitz sequences, respectively. It will be appreciated that the equivalent residues in other Rhomboid and substrate polypeptides may have a different position and number, because of differences in the amino acid sequence of each polypeptide. These differences may occur, for example, through variations in the length of the N terminal domain. Equivalent residues in other Rhomboid and substrate polypeptides are easily recognisable by their overall sequence context and by their positions with respect to the TMDs.

A polypeptide which is a member of the Rhomboid family preferably comprises residues R152, G215, S217 and H281, more preferably residues W151, R152, N169, G215, S217 and H281. The presence of these conserved residues may be used to identify Rhomboid polypeptides in other protozoan pathogens.

Preferably, a Rhomboid polypeptide comprises at least 4 TMDs, more preferably at least 5 TMDs, with residues N169, S217 and H281 each occurring in different TMD at about the same level in the lipid membrane bilayer.

Preferred Rhomboid polypeptides comprise a GxSx motif, for example GxSG.

A Rhomboid polypeptide may also comprise additional amino acid residues which are heterologous to the Rhomboid sequence. For example, a Rhomboid polypeptide or fragment thereof may be included as part of a fusion protein, e.g. including a binding portion for a different ligand.

Whilst Rhomboid polypeptides may share relatively low overall sequence identity, they are reliably identified by bioinformatics techniques and manual inspection of key residues, as described herein.

A polypeptide which is a member of the Rhomboid family (i.e. a Rhomboid polypeptide) may be identified by the presence of a Rhomboid homology domain, as defined by the PFAM protein structure annotation project (Bateman A. et al (2000) The Pfam Protein Families Database Nucl. Acid. Res. 28 263-266). The Pfam rhomboid homology domain is built from a Hidden Markov Model (HMM) using 83 rhomboid sequences as a seed. The Pfam 'rhomboid' domain has the pfam specific accession number PF01694.

Various other methods suitable for use in identifying Rhomboid polypeptides are known in the art.

Particularly valuable methods include the use of Hidden Markov Models built from groups of previously identified Rhomboid proteins, including, but not limited to *Drosophila* Rhomboids 1-4. Such bio-informatics techniques are well known to those skilled in the art (Eddy S. R. Curr. Opin. Struct. Biol. 1996 6(3) 361-365).

Rhomboid polypeptides are preferably able to proteolytically cleave one or more of *Drosophila* proteins Spitz, Keren and Gurken or protozoan proteins such as Amal and CTRP, but not similar type I transmembrane proteins like TGFA, Delta, EGFR, and TGN38.

Suitable substrate polypeptides are Type 1 membrane proteins with a single TMD orientated with an N terminal extracellular/lumenal domain. A substrate polypeptide may comprise a transmembrane domain which has a lumen proximal region having one or more of the residues of residues 138-144 of the *Drosophila* Spitz sequence SEQ ID NO: 1 (ASIASGA), or a luminal region having an equivalent conformation, structure or three dimensional arrangement to that of residues 138-144 of the *Drosophila* Spitz sequence SEQ ID NO: 1 (ASIASGA).

In preferred embodiments, residues 1 to 7 of the TMD of a substrate polypeptide are not hydrophobic.

A substrate polypeptide may comprise a G residue within the portion of the TMD proximal to the lumenal or extracellular domain of the polypeptide (i.e. between residues 1 and 8 of the TMD), preferably, the G residue being at a position equivalent to Spitz G143 (i.e. the $6^{th}$ residue of the TMD). Preferably, a substrate polypeptide comprises a GA or GG motif within the portion of the TMD proximal to the lumenal or extracellular domain of the polypeptide (i.e. between residues 1 and 8 of the TMD), preferably at positions equivalent to G143 and A144 of the Spitz sequence (i.e the $6^{th}$ and $7^{th}$ residues of the TMD).

A substrate polypeptide may further comprise a triplet motif of small amino acid residues at positions equivalent to A138, S139 and I140 of Spitz (i.e. the $1^{st}$, $2^{nd}$ and $3^{rd}$ residues of the TMD as numbered from the N terminal (extracellular) boundary of the TMD). Small residues include Gly, Ala, Ser, Ile, Leu, Val and Thr. Suitable motifs at this position include motifs which have Ala at a position equivalent to Spitz A138, such as AGG and ASI. The presence of Phe at positions 1, 2 or 3 of the TMD of a polypeptide is a counter-indication for the polypeptide being a Rhomboid substrate (i.e. such a polypeptide is unlikely to be efficiently cleaved by a Rhomboid polypeptide).

Suitable substrate polypeptides may include protozoan adhesive micronemal polypeptides. An adhesive micronemal polypeptide may be from a protozoan pathogen, for example an Apicomplexan pathogen. Suitable adhesive micronemal polypeptides include transmembrane proteins that belong to the thrombospondin-related-anonymous proteins (TRAPs) family.

A protozoan adhesive micronemal polypeptide which is a suitable substrate may include an AGG or AGL motif at residues 1, 2 and 3 of the TMD as described above and a GG motif at positions 6 and 7 of the TMD.

The protozoan pathogen may a member of the *Apicomplexa* family, for example an apicomplexan pathogen selected from the group consisting of *Plasmodium, Toxoplasma, Eimeria, Sarcocystis, Babesia, Isospora, Cyclospora* and *Cryptosporidium*, for example *P. falciparum, P. bergei, T. gondii, C. parvum, E. tenella, S. muris, Babesia bovis, Cyclospora belli, Theileria annulata* or *Theileria parva*.

Examples of suitable polypeptides include AMA1, MIC2, MIC6, MIC8, MIC12, (from *T. gondii*), AMA1, TRAP, CTRP (from *P. falciparum* and *P. berghei*), MIC1 and MIC4 (from *E. tenella*) or other polypeptide as shown in Table 2.

In some preferred embodiments, the substrate polypeptide may be CTRP or AMA1, for example *P. falciparum* CTRP or AMA1

The substrate polypeptide and the Rhomboid polypeptide may each comprise an ER (endoplasmic reticulum) retention signal. For example, a rhomboid polypeptide may comprise a C terminal (lumenal) KDEL motif and a substrate may comprise a C terminal (cytoplasmic) KKXX motif (Jackson et al (1993) J. Cell Biol. 121(2) 317-333)

The substrate polypeptide may comprise a detectable label, such as green fluorescent protein (GFP), luciferase or alkaline phosphatase. This is preferably located in the soluble extracellular domain, allowing convenient detection of the soluble cleaved product and is particularly useful in automated assays.

Methods for obtaining or identifying modulators, in particular inhibitors, of protozoan pathogen infectivity may be cell-based or non-cell-based.

In non-cell based methods, the rhomboid polypeptide and the substrate polypeptide may be isolated or contained in a liposome. Liposome based assays may be carried out using methods well-known in the art (Brenner C. et al (2000) Meths in Enzymol. 322 243-252, Peters et al (2000) Biotechniques 28 1214-1219, Puglielli, H. and Hirschberg C. (1999) J. Biol. Chem. 274 35596-35600, Ramjeesingh, M. (1999) Meths in Enzymol. 294 227-246).

Preferably, methods according to the present invention take the form of cell based methods. A cell based method may be performed in a cell such as a protozoan cell (e.g. a Toxoplasma cell), a yeast strain, insect or mammalian cell line such as CHO, HeLa and COS cells, in which the relevant polypeptides or peptides are expressed from one or more vectors introduced into the cell.

In a preferred embodiment, the Rhomboid polypeptide and the substrate polypeptide may be expressed in a host cell from heterogeneous encoding nucleic acid.

Nucleic acid encoding the Rhomboid polypeptide and the substrate polypeptide may be contained on a single expression vector or on separate expression vectors.

Persons skilled in the art may vary the precise format of methods of the invention using routine skill and knowledge. For example, in some embodiments, the cleaved GFP moiety of a GFP-substrate fusion may be captured with an anti-GFT antibody (Santa Cruz Biologicals), washed and then the captured GFP detected with a polyclonal or monoclonal antibody conjugated to an enzyme (capture ELISA) or a fluorescent label.

Some embodiments may employ an ELISA format in which, for example, a suitable polyclonal anti-GFP conjugated to horse-radish peroxidase or to alkaline phosphatase may be used. Such a conjugate is preferred since the number of incubations required is reduced. Alternatively, a biotinylated anti-GFP antibody in combination with an avidin or streptavidin enzyme conjugate may be used.

In other embodiments, fluorescence detection may be used, for example using a Europium- or Terbium-labelled antibody or streptavidin e.g. Delphia or Lance reagents, Perkin Elmer). These labels show a long fluorescence lifetime and have improved signal:noise ratio characteristics.

In other embodiments, GFP may be replaced in the GFP-substrate construct with a different enzyme label at the N-terminus to give a direct assay for the cleaved substrate in the medium (or the label may be added to such a construct). Suitable enzymes include Renilla luciferase (Lui, J., and Escher, A. (1999) Gene 237, 153-159) and secretable alkaline phosphatase sequence (SEAP) (Clontech).

It is not necessary to use the entire full-length proteins for in vitro or in vivo assays of the invention. Polypeptide fragments as described herein which retain the activity of the full length protein may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods, which are well known in the art. Another approach is to synthesise a nucleic acid comprising all or part of the coding sequence from a series of synthetic oligonucleotides. The coding sequence may be synthesised using a more optimal genetic code for the host cells (Kocken C H et al Infect Immun. (2002) 70(8): 4471-6), for example reflecting mammalian codon usage for expression in mammalian cells.

A Rhomboid polypeptide fragment may consist of fewer amino acid residues than said full-length polypeptide. Such a fragment may consist of 325 amino acids or less, 300 amino acids or less, or 275 amino acids or less and/or may consist of at least 100 amino acids, more preferably at least 150, 200, 250 or 300 amino acids. A suitable fragment may comprise five TMDs.

Such a fragment preferably comprises residues equivalent to R152, G215, S217 and H281, more preferably residues W151, R152, N169, G215, S217 and H281 of the *Drosophila* Rhomboid-1 sequence (Acc No: P20350), which are important for the catalytic activity of the protein and are highly conserved in the Rhomboid family.

A substrate polypeptide fragment comprises fewer residues than the full-length polypeptide and preferably comprises the transmembrane domain of the polypeptide. The TMD may be conveniently identified using commercially available software such as TMHMM (Krogh A. et al (2001) J. Mol. Biol. 305 567-580) and TmPred (Hofmann K & Stoffel W (1993) Biol Chem. Hoppe Seyler 374 166).

In some embodiments, a chimeric substrate polypeptide may be used which comprises a substrate polypeptide TMD which is cleavable by a Rhomboid polypeptide and heterogeneous intra- and extra-cellular domains.

Combinatorial library technology (Schultz, J S (1996) Biotechnol. Prog. 12: 729-743) provides an efficient way of testing a potentially vast number of different substances for ability to modulate activity of a polypeptide. Prior to or as well as being screened for modulation of activity, test substances may be screened for ability to interact with the Rhomboid polypeptide, e.g. in a yeast two-hybrid system (which requires that both the polypeptide and the test substance can be expressed in yeast from encoding nucleic acid). This may be used as a coarse screen prior to testing a substance for actual ability to modulate protease activity of the polypeptide.

The amount of test substance or compound, which may be added in a method of the invention, will normally be determined by trial and error depending upon the type of compound used. Typically, from about 0.01 to 100 µM. concentrations of putative inhibitor compound may be used, for example from 0.1 to 10 µM.

Test compounds may be natural or synthetic chemical compounds used in drug screening programmes. Extracts of plants that contain several characterised or uncharacterised components may also be used.

Methods of the invention may comprise the step of identifying the test compound as an inhibitor of adhesive micronemal polypeptide cleavage.

One class of putative inhibitor compounds can be derived from the Rhomboid polypeptide and/or substrate polypeptide (e.g. adhesive micronemal polypeptide). Peptide fragments of from 5 to 40 amino acids, for example, from 6 to 10 amino acids may be tested for their ability to disrupt such interaction or activity.

The inhibitory properties of a peptide fragment as described above may be increased by the addition of one of the following groups to the C terminal: chloromethyl ketone, aldehyde and boronic acid. These groups are transition state analogues for serine, cysteine and threonine proteases. The N terminus of a peptide fragment may be blocked with carbobenzyl to inhibit aminopeptidases and improve stability (Proteolytic Enzymes 2nd Ed, Edited by R. Beynon and J. Bond Oxford University Press 2001).

Antibodies directed to the site of interaction in the protozoan Rhomboid polypeptide or adhesive micronemal protein form a further class of putative inhibitor compounds.

Candidate inhibitor antibodies may be characterised and their binding regions determined to provide single chain antibodies and fragments thereof which are responsible for disrupting the interaction.

Antibodies may be obtained using techniques that are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art,.and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed, the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of. the VL, VH, Cl and CHl domains; the Fd fragment consisting of the VH and CHl domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion that encodes antibody and reporter molecule. The mode of determining binding is not a feature of the present invention and those skilled in the art are able to choose a suitable mode according to their preference and general knowledge.

Antibodies may also be used in purifying and/or isolating Rhomboid and adhesive micronemal polypeptides for use in the present methods, for instance following production of the polypeptide or peptide by expression from encoding nucleic acid therefor.

Antibodies may be useful in a therapeutic context (which may include prophylaxis) to disrupt Rhomboid mediated cleavage of adhesive micronemal proteins and thus to reduce pathogen invasiveness in the treatment protozoan infections, including malaria.

Antibodies may also be employed in accordance with the present invention for other therapeutic and non-therapeutic purposes which are discussed elsewhere herein.

As described above, adhesive micronemal polypeptide cleavage is an essential step in the infection of host cells by protozoan pathogens. Compounds which inhibit adhesive micronemal polypeptide cleavage may thus be useful in inhibiting protozoan pathogen invasiveness.

Methods of the invention may further comprise the step of determining the ability of said test compound to inhibit the invasiveness of a protozoan pathogen.

This may be achieved by contacting a host cell with a protozoan pathogen in the presence of the test compound under conditions in which the pathogen normally infects the host cell.

Invasiveness of a protozoan pathogen may be determined, for example, in the presence and absence of test compound, in tissue culture using hepatocytes or HepG2 cells. Alternatively, the ability of a sporozoite to glide on a glass slide may be determined. This motility is tightly linked to invasiveness (Matuschewski K et al EMBO J (2002) 21 (7) 1597-1606).

In other assay systems, sporozoites may be injected into an animal model (e.g. rat) to which a test compound is administered and the extent or amount of infection of hepatocytes within the animal determined, and compared to control animals (Matuschewski K et al supra). Determination of hepatocyte infection may involve sacrificing and dissecting the animal model.

A decrease or reduction in the rate of infection in the presence relative to the absence of test compound is indicative that the test compound inhibits infectivity.

The test compound may further be isolated and/or manufactured/synthesised and subsequently formulated into a pharmaceutical composition with a pharmaceutically acceptable excipient, vehicle or carrier.

It is desirable that compounds for use in therapeutic contexts preferentially or specifically inhibit protozoan Rhomboid polypeptide relative to human Rhomboid polypeptide. Methods of the invention may include a further screen to identify such compounds.

A method may therefore comprise the further step of;
bringing into contact an isolated human Rhomboid polypeptide and a polypeptide substrate in the presence of the test compound; and,
determining proteolytic cleavage of the substrate by the human Rhomboid polypeptide.

A human Rhomboid polypeptide may be selected from the group consisting of Human RHBDL-1 (Human Rhomboid-1: Pascall and Brown (1998) FEBS Lett. 429, 337-340), Human RHBDL-2 (NM_017821) and Human RHBDL-3.

Suitable polypeptide substrates for human Rhomboids are described above and are cleaved by the Rhomboid polypeptide within the transmembrane domain.

A suitable substrate polypeptide may comprise a transmembrane motif which has one or more residues of the *Drosophila* Spitz ASIASGA motif within the region proximal to the lumenal or extracellular domain of the polypeptide (i.e. residues 1 to 8 of the TMD starting at the lumenal boundary) or may comprise a transmembrane motif which none of the residues of the *Drosophila* Spitz ASIASGA motif, but which instead possess a motif having an equivalent structure which is cleaved by Rhomboid polypeptide (e.g. Gurken or other sequence shown in FIG. 1). Preferably a substrate polypeptide comprises one or both of motifs described above in the region proximal to the lumenal or extracellular domain of the polypeptide.

Following identification of a compound using a method of the invention described herein, a method may further comprise modifying the compound to optimise the pharmaceutical properties thereof.

The modification of a 'lead' compound identified as biologically active is a known approach to the development of pharmaceuticals and may be desirable where the active compound is difficult or expensive to synthesise or where it is unsuitable for a particular method of administration, e.g. peptides are not well suited as active agents for oral compositions as they tend to be quickly degraded by proteases in the alimentary canal. Modification of a known active compound (for example, to produce a mimetic) may be used to avoid randomly screening large number of molecules for a target property.

Modification of a 'lead' compound to optimise its pharmaceutical properties commonly comprises several steps. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR.

Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the optimisation of the lead compound.

A template molecule is then selected onto which chemical groups that mimic the pharmacophore can be grafted. The template molecule and the chemical groups grafted on to it can conveniently be selected so that the modified compound is easy to synthesise, is likely to be pharmacologically acceptable, and does not degrade in vivo, while retaining the biological activity of the lead compound. The modified compounds found by this approach can then be screened to see whether they have the target property, or to what extent they exhibit it. Modified compounds include mimetics of the lead compound.

Further optimisation or modification can then be carried out to arrive at one or more final compounds for in vivo or clinical testing.

Rhomboid and adhesive miconemal polypeptides may also be used in methods of designing mimetics which are suitable for inhibiting protozoan pathogen infectivity.

The present invention provides a method of designing mimetics having the biological activity of inhibiting the Rhomboid mediated cleavage of adhesive miconemal polypeptides and thus inhibiting protozoan pathogen invasiveness, said method comprising:

(i) analysing a compound having the biological activity to determine the amino acid residues essential and important for the activity to define a pharmacophore; and, (ii) modelling the pharmacophore to design and/or screen candidate mimetics having the biological activity.

A suitable compound may be, for example, a protozoan Rhomboid polypeptide or fragment as described herein.

Suitable modelling techniques are known in the art. This includes the design of so-called "mimetics" which involves the study of the functional interactions of the molecules and the design of compounds which contain functional groups arranged in such a manner that they could reproduced those interactions.

The modelling and modification of a 'lead' compound to optimise its properties, including the production of mimetics, is described above.

The activity or function of a protozoan Rhomboid polypeptide may be inhibited, as noted, by means of a compound that interferes in some way with the interaction of protozoan Rhomboid with adhesive micronemal polypeptides or other suitable substrate polypeptides. An alternative approach to inhibition employs regulation at the nucleic acid level to inhibit activity or function by down-regulating production of protozoan Rhomboid.

For instance, expression of a gene may be inhibited using anti-sense or RNAi technology. The use of these approaches to down-regulate gene expression is now well-established in the art.

Anti-sense oligonucleotides may be designed to hybridise to the complementary sequence of nucleic acid, pre-mRNA or mature mRNA, interfering with the production of Rhomboid polypeptide so that its expression is reduced or completely or substantially completely prevented. In addition to targeting coding sequence, antisense techniques may be used to target control sequences of a gene, e.g. in the 5' flanking sequence, whereby the antisense oligonucleotides can interfere with expression control sequences. The construction of antisense sequences and their use is described for example in Peyman and Ulman, Chemical Reviews, 90: 543-584, (1990) and Crooke, Ann. Rev. Pharmacol. Toxicol., 32: 329-376, (1992).

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g. about 15, 16 or 17.

An alternative to anti-sense is to use a copy of all or part of the target gene inserted in sense, that is the same, orientation as the target gene, to achieve reduction in expression of the target gene by co-suppression; Angell & Baulcombe (1997) The EMBO Journal 16, 12: 3675-3684; and Voinnet & Baulcombe (1997) Nature 389: pg 553). Double stranded RNA (dsRNA) has been found to be even more effective in gene silencing than both sense or antisense strands alone (Fire A. et al Nature, 391, (1998)) and has been used effectively in *Plasmodium* (Malhotra P et al Mol. Microb. (2002) 45(5) 1245-1254; McRobert L et al Mol. Biochem. Parasitol. (2002) 119(2) 273-278). dsRNA mediated silencing is gene specific and is often termed RNA interference (RNAi).

RNA interference is a two step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir S M. et al. Nature, 411, 494-498, (2001)).

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, *Cancer Gene Therapy*, 2(3): 213-223, and Mercola and Cohen, 1995, *Cancer Gene Therapy*, 2(1), 47-59.

Thus, a modulator of protozoan Rhomboid activity and thus a modulator of protozoan pathogen infectivity may comprise a nucleic acid molecule comprising all or part of a Rhomboid coding sequence shown in Table 1 or the complement thereof Such a molecule may suppress the expression of protozoan Rhomboid polypeptide and may comprise a sense or anti-sense Rhomboid coding sequence or may be a Rhomboid specific ribozyme, according to the type of suppression to be employed.

The type of suppression will also determine whether the molecule is double or single stranded and whether it is RNA or DNA.

Another aspect of the present invention provides a method of producing a pharmaceutical composition comprising;
   identifying a compound which inhibits the invasiveness of a protozoan pathogen using a method described herein; and,
   admixing the compound identified thereby with a pharmaceutically acceptable carrier.

As described above, a method of the invention may comprise the step of modifying the compound to optimise the pharmaceutical properties thereof.

Another aspect of the invention provides a method for preparing a pharmaceutical composition for treating a protozoan pathogen infection comprising;
   i) identifying a compound which modulates the proteolytic activity of a Rhomboid polypeptide,
   ii) synthesising the identified compound, and;
   iii) incorporating the compound into a pharmaceutical composition.

The identified compound may be synthesised using conventional chemical synthesis methodologies. Methods for the development and optimisation of synthetic routes are well known to a skilled person.

The compound may be modified and/or optimised as described above.

Incorporating the compound into a pharmaceutical composition may include admixing the synthesised compound with a pharmaceutically acceptable carrier or excipient.

Another aspect of the invention provides a compound which modulates protozoan pathogen infectivity obtained by a method as described herein. Such a compound may comprise or consist of a peptide fragment of a protozoan Rhomboid polypeptide.

Another aspect of the invention provides a pharmaceutical composition comprising a compound which modulates the proteolytic activity of a Rhomboid polypeptide obtained by a method described herein.

In other aspects the invention provides the use of a compound obtained by a method described herein in the manufacture of a composition for treatment of a protozoan pathogen infection and a method comprising administration of a composition obtained by a method described herein to a patient for treatment of a protozoan pathogen infection.

Protozoan pathogens are described above. Disorders associated with infection with a protozoan pathogen include malaria, toxoplasmosis, cryptosporidosis, diarrhoea associated with *Isospora belli* or *Cyclospora cayetanis* infection, and various livestock disorders associated with *Eimeria* infection.

Whether it is a polypeptide, antibody, peptide, anti-sense, sense or siRNA nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

Another aspect of the invention provides a method of identifying a protozoan Rhomboid polypeptide comprising,
(a) providing a test Rhomboid polypeptide,
(b) bringing into contact a substrate polypeptide and the test Rhomboid polypeptide under conditions in which the substrate polypeptide is normally proteolytically cleaved; and,
(c) determining cleavage of the substrate polypeptide.

A suitable test Rhomboid polypeptide may comprise an amino acid sequence encoded by a nucleic acid sequence shown in Table 1. Screening databases may identify other suitable test Rhomboid polypeptides, in particular, databases of protozoan nucleic acid sequence, using the bioinformatics techniques discussed above.

Suitable substrate polypeptides include protozoan adhesive micronemal polypeptides. A suitable adhesive micronemal polypeptide may belong to the thrombospondin-related-anonymous proteins (TRAPs) family. Examples of suitable polypeptides include AMA1, MIC2, MIC6, MIC8, MIC12, (from *T. gondii*), TRAP, CTRP (from *P. falciparum* and *P. berghei*), MIC1 and MIC4 (from *E. tenella*) or fragments thereof which comprise the transmembrane domain. In particular, CTRP and/or AMA1 may be used.

Other aspects of the invention relate to protozoan Rhomboid polypeptides and encoding nucleic acids.

An aspect of the invention provides a protozoan Rhomboid polypeptide which proteolytically cleaves the transmembrane domain of an adhesive micronemal polypeptide.

Such a polypeptide,may have a sequence encoded by a nucleic acid sequence shown in Table 1 (for example Pf Rho1-7) or may be a fragment of such a sequence which consists of fewer residues than the full-length protozoan Rhomboid polypeptide.

The KDEL ER retention sequence is not found in natural protozoan Rhomboid polypeptides and directs the expressed Rhomboid polypeptide to be retained the ER (endoplasmic reticulum) rather than the micronemes of the protozoan cell. As described below, Rhomboid polypeptides labelled with an ER retention sequence such as KDEL may be particularly useful in certain embodiments of the invention, as proteolyic cleavage by such polypeptides avoids potential problems with variations in secretion efficiency.

An aspect of the invention thus provides an isolated protozoan Rhomboid polypeptide as described herein comprising a C terminal ER retention sequence. A suitable retention sequence consists of the amino acid sequence KDEL.

Another aspect of the invention provides an isolated nucleic acid encoding a protozoan Rhomboid polypeptide as described above.

The coding sequence may be a nucleic acid sequence listed in Table 1 or it may be a mutant, variant, derivative or allele of a sequence listed. The sequence may differ from a sequence of Table 1 by a change, which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from a sequence listed in Table 1 yet encode a polypeptide with the same amino acid sequence. As described above, codon usage may be adjusted in order to express an amino acid sequence in a particular host system, such as a mammalian cell.

An isolated nucleic acid may share greater than about 10% sequence identity with a nucleic acid sequence of Table 1 greater than 20%, greater than 30%, greater than 40%, greater than 50%, greater than 60%, greater than about 70%, greater than about 80%, greater than about 90%, or greater than about 95%.

The present invention also extends to nucleic acid that hybridizes with a sequence listed in Table 1 under stringent conditions. Suitable conditions include, e.g. for sequences that are about 80-90% identical; hybridisation overnight at 42° C. in 0.25 M $Na_2HPO_4$, pH 7.2, 6.5% SDS, 10% dextran sulfate and a final wash at 55° C. in 0.1×SSC, 0.1% SDS. For sequences that are greater than about 90% identical, suitable conditions include. hybridization overnight at 65° C. in 0.25M $Na_2HPO_4$, pH 7.2, 6.5% SDS, 10% dextran sulfate and a final wash at 60° C. in 0.1×SSC, 0.1% SDS.

A convenient way of producing a polypeptide for use in assays and methods according to the present invention is to express nucleic acid encoding it, by use of the nucleic acid in an expression system. Accordingly, the present invention also encompasses a method of making a polypeptide (as disclosed), the method including expression from nucleic acid encoding the polypeptide and testing for Rhomboid protease activity. This may conveniently be achieved by growing a host cell in culture, containing such a vector, under appropriate conditions that cause or allow expression of the polypeptide. Polypeptides may also be expressed in in vitro systems, such as reticulocyte lysate.

Another aspect of the present invention therefore provides a method of producing a Rhomboid polypeptide comprising:
  (a) causing expression from nucleic acid which encodes a protozoan Rhomboid polypeptide in a suitable expression system to produce the polypeptide recombinantly;
  (b) testing the recombinantly produced polypeptide for Rhomboid protease activity.

Suitable nucleic acid sequences include a nucleic acid sequence encoding a protozoan rhomboid polypeptide a mutant, variant or allele thereof as described herein.

A polypeptide may be isolated and/or purified (e.g. using an antibody) for instance after production by expression from encoding nucleic acid (for which see below). Thus, a polypeptide may be provided free or substantially free from contaminants with which it is naturally associated (if it is a naturally-occurring polypeptide). A polypeptide may be provided free or substantially free of other polypeptides.

The recombinantly produced polypeptide may be isolated and/or tested for Rhomboid protease activity by determination of the cleavage of a substrate polypeptide such as an adhesive micronemal polypeptide upon incubation of the polypeptide with the substrate polypeptide.

An isolated nucleic acid as described herein, for example a nucleic acid encoding a protozoan Rhomboid polypeptide, may be comprised in a vector. Such a vector may further include a nucleic acid sequence encoding a substrate polypeptide such as a protozoan adhesive micronemal protein. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Systems for cloning and expression of a polypeptide in a variety of different host cells are well known. Suitable host cells include bacteria, eukaryotic cells such as mammalian and yeast, baculovirus and protozoan systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Further aspects of the invention provide a host cell containing heterologous nucleic acid encoding a protozoan Rhomboid polypeptide, including a Rhomboid polypeptide which has a KDEL tag or which is a fragment of a full length Rhomboid sequence, and a host cell containing heterologous nucleic acid encoding a protozoan Rhomboid polypeptide and a substrate polypeptide, for example a protozoan adhesive micronemal polypeptide. Nucleic acid encoding the protozoan Rhomboid polypeptide and substrate polypeptide may be present on a single nucleic acid construct or vector within the host cell or nucleic acid encoding the two polypeptides may be present on separate constructs or vectors.

The nucleic acid may be integrated into the genome (e.g. chromosome) of the host cell. Integration may be promoted by inclusion of sequences that promote recombination with the genome, in accordance with standard techniques. The nucleic acid may be on an extra-chromosomal vector within the cell.

The introduction of nucleic acid into a host cell, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced.

A Rhomboid polypeptide may be co-expressed in a host cell with a substrate polypeptide, such as a protozoan adhesive micronemal polypeptide, and the Rhomboid serine protease activity determined by determining cleavage of the substrate polypeptide. Cleavage may be determined by determining the presence or absence of soluble cleavage products which may be secreted into the culture medium.

Aspects of the present invention will now be illustrated with reference to the following experimental exemplification, by way of example and not limitation. Further aspects and embodiments will be apparent to those of ordinary skill in the art. All documents mentioned in this specification are hereby incorporated herein by reference.

FIG. 1 shows an alignment of transmembrane domains of micronemal proteins from apicomplexan species with *Drosophila* Spitz and Keren. All are single-pass type 1 transmembrane proteins. Black lines indicate the predicted TMD regions: the line above the sequences predicts the micronemal protein TMDs; the line below predicts the TMDs of Spitz and Keren. The GA or GG motif approximately seven residues into the TMD (double underline) and the conserved small residues near the luminal/extracellular face of the TMD (single underline) are essential for rhomboid cleavage of Spitz and are underscored. Note also the conserved tyrosine (Y) at the cytoplasmic face of the TMDs. Accession numbers of the sequences are shown in Table 2.

Table 1a shows examples of *Plasmodium falciparum* rhomboids which were initially identified by the Pfam motif-finding algorithm, with a score of greater than 10. Four annotations are listed: sequencing consortium annotation (Sanger), plus 3 automatic gene prediction algorithms, FullPhat, GlimmerM and Genefinder. The approximate position on the chromosome is also provided along with the predicted sequence around the rhomboid active site. Rhomboids 2 and 5 are predicted to be mitochondrial, based on the existence of a mitochondrial targeting sequence predicted by MitoProt or Predotar. These genes represent the most reliable prediction of true rhomboids in the published *P. falciparum* genome sequence as predicted by the Pfam motif-finding algorithm, with a score of greater than 10.

Table 1b shows an example of a candidate *Toxoplasma gondii* rhomboid (ref: http://ParaDB.cis.upenn.edu/toxo/index.html)

Table 2 shows examples of substrates for rhomboid proteases from apicomplexan species.

EXPERIMENTAL

Identification of *Plasmodium* Rhomboid Polypeptides.

The published *Plasmodium* genome sequence was searched for Rhomboids polypeptides using PFAM as described above, selecting scores higher than 10, followed by visual inspection to identify key Rhomboid residues.

A number of putative Rhomboids were identified using PFAM. These were further analysed for the presence of residues equivalent to residues N169, G215, S217 and H281 of *Drosophila* Rhomboid-1, which are required for catalytic activity. Candidates identified as being within the subclass of mitochondrial rhomboids were also excluded by prediction of the existence of a mitohondrial targeting sequence with PREDOTAR algorithm (www.inra.fr/predotar) or MitoProt (Claros M., et al Eur. J. Biochem. (1996) 241 779-786)

Rhomboid polypeptides identified by this approach are listed in Table 1.

Cloning of *Plasmodium* Rhomboid

Rhomboid coding sequences were amplified by PCR from *Plasmodium* cDNA using the protocols set out in Sambrook & Russell Molecular Cloning, A Laboratory Manual, 3$^{rd}$ Edition, Cold Spring Harbor Laboratory Press, 2001, and Ausubel et al, Short Protocols in Molecular Biology, John Wiley and Sons, 1992. The amplified sequences were then inserted into a pcDNA3.1 (Invitrogen).

The Pf Rho 1, 3, 4 and 7 genes were resynthesised (Geneart, DE) with codon usage adjusted as described in Kocken et al (2002) Infect Immun 70(8) 4471-4476 to optimise expression in mammalian cell lines.

Expression of Pf rhomboids-1, -3 and -7 was observed in COS cells.

Cloning of Adhesive Micronemal Proteins of *Plasmodium*

Oligonucleotide primers for amplification of the adhesive micronemal proteins Ama-1 and CTRP of *Plasmodium* were designed based on the published sequences using conventional primer design software.

The coding sequences were amplified using PCR in accordance with standard techniques, and cloned into a standard mammalian expression vector for expression in cell culture. The coding sequences incorporated a triple-HA tag to facilitate detection. Expression was detected by conventional Western blotting techniques using available anti-HA antibodies (Roche).

*Plasmodium* Rhomboid Activity

*Plasmodium* rhomboid activity was determined using published methods described in Urban et al Cell (2001) 107(2): 173-82 and WO02/093177.

Briefly, Pf rhomboids-1 and -3 were co-expressed with GFP-tagged Spitz under control of a CMV promoter; as follows; COS cells were grown in DMEM medium (supplemented with 10% foetal calf serum), and transfected with FuGENE 6 Transfection Reagent (Roche).

Cells were co-transfected in 35 mm culture wells with 25-250 ng of (a) rhomboid construct comprising the Pf-rhomboid-1 or -3 coding sequence inserted into the vector pcDNA 3.1+ (Invitrogen), and (b) substrate construct comprising the GFP-Spitz coding sequence inserted into pcDNA 3.1+ (Invitrogen).

Empty plasmid was used to bring the total DNA to 1 µg per well.

Construct (b) was transfected into COS cells in the absence of construct (a) as a control for endogenous cleavage of the substrate.

24-30 hours post-transfection, the medium was replaced with serum-free medium; this was harvested 24 hours later and cells were lysed in SDS-sample buffer.

For some experiments, the serum-free medium was supplemented with the metalloprotease inhibitor batimastat (British Biotech) or ilomostat (Calbiochem) to minimize endogenous substrate cleavage in the assay. For inhibitor assays, a test compound may be included in the serum-free medium.

Spitz cleavage was assayed by detecting the accumulation of the GFP-tagged Spitz extracellular domain in the medium by standard western blotting techniques, using an anti-GFP antibody(Santa Cruz Biologicals).

Parallel experiments were also performed using a C-terminally tagged form of Spitz. Cleavage of the C-terminal tagged Spitz was assayed by detecting the intracellular cleaved product in western blots of cell extracts.

Both Pf rhomboid-1 and -3 were observed to show specific cleavage of Spitz, which was not inhibited by batimastat. Batimastat is a potent inhibitor of metalloproteases that can cause non-specific shedding of cell surface proteins. These results show that both Pf rhomboid-1 and -3 are active rhomboid proteases that can recognise 'Spitz-like' TMDs.

Cleavage of Pf Adhesion Protein Ama-1

Pf adhesion protein Ama-1 was recoded with a mammalian codon usage profile to allow for expression in mammalian cells.

Cleavage of Ama-1 by *Drosophila* Rhomboid-1 was determined using the method'set out above. Briefly, Ama-1 and *Drosophila* Rhomboid-1 were co-expressed as described above in COS cells using the CMV promoter for both constructs. Standard western blotting techniques using an anti-Ama-1 antibody were employed to detect the accumulation of the extracellular domain of cleaved Ama-1 in the COS cell medium.

Efficient cleavage of Ama-1 by *Drosophila* Rhomboid-1 was observed. This cleavage was not sensitive to batimastat. This shows that Ama-1 has a rhomboid-cleavable TMD.

Cleavage of Pf Adhesion Protein CTRP

Cleavage of the CTRP TMD by *Drosophila* Rhomboid-1 was also determined using the methods described above.

Briefly, *Drosophila* Rhomboid-1 was co-expressed as described above in COS cells with a chimeric protein comprising (from N- to C-terminus) the signal peptide of Spitz, followed by GFP, followed by the Pf CTRP transmembrane domain, followed by the cytoplasmic domain of TGFalpha (i.e. the CTRP TMD with heterologous extracellular and cytoplasmic domains). The CMV promoter was used to express both constructs.

Cleavage of the CTRP TMD was assayed by the standard technique described above. If the CTRP TMD is cleaved by the Rhomboid protein, GFP accumulates in the medium of the transfected cells in a batimastat-insensitive manner. Accumulated GFP is then detected with an anti-GFP antibody (Santa Cruz Biologicals) as described above.

It was observed that the TMD from Pf adhesion protein CTRP is cleaved efficiently by *Drosophila* rhomboid-1.

Expression of Rhomboid in *Plasmodium*

Pairs of amplification primers specific for each *P. falciparum* Rhomboid were designed using conventional primer design software. The expression of *Plasmodium* Rhomboid proteins was analysed by performing PCR on cDNA prepared from RNA isolated from the blood stage of *Plasmodium falciparum* using standard techniques.

Rhomboids-1, -3, -4 and -6 are all observed to be expressed in blood stage *Plasmodium* parasites.

*Plasmodium* Rhomboids are therefore present at the blood cell invasion stage of the parasitic life-cycle and may play a key role in mediating this invasion.

In Vivo Role of Rhomboids in Infectivity of Parasites

Mutant strains of *P. falciparum* are generated in which the candidate rhomboid protein is knocked out. The infectiousness of the mutant parasite is then determined.

The knockout is done either by standard targeted gene disruption (Sultan et al Cell 90 511) or, more conveniently, by RNA interference (RNAi), as described below.

100 μg of RNA corresponding to each candidate Rhomboid gene is synthesized by in vitro transcription from 5 μg linearized plasmid templates according to manufacturer's instructions (Promega Ribomax system). The resulting RNA is purified using the RNeasy protocol (Qiagen), denatured by boiling, and annealed in 1 mM Tris-HCl pH7.4, 1 mM EDTA overnight. The resulting dsRNA is then added to a culture of *P. falciparum* sporozoites (Malhotra et al Mol. Microb. 45 1245-1254).

The reduced infectivity or gliding behaviour of the knockout parasites relative to the wild-type controls confirms that rhomboid regulates the infectious process.

Impairment of the proteolysis of the adhesive micronemal proteins may also be established in the rhomboid mutant (or RNAi) cells, by determining the production of cleaved product by Western blotting using anti-TRAP antibodies (Sharma et al Infection & Immunity 64 2172-2179, Gantt et al Infection & Immunity 68 3667-3673).

TABLE 1a

| Sanger | FullPhat | GlimmerM | Genefinder | Chromosome | Approx location | Motif | Rhomboid |
|---|---|---|---|---|---|---|---|
| PFE03040c | chr5.phat_92 | chr5.glm_74 | chr5.gen_274 | 5 | 289 kb | GSSG | Rho1 |
| PFE0755c | chr5.phat_172 | chr5.glm_161 | chr5.gen_236 | 5 | 624 kb | GASG | Rho2 (mito) |
| PF11_0150 | chr11.phat_164 | chr11.glm_163 | Not predicted | 11 | 538 kb | GAST | Rho3 |
| PF13_0312 | chr13.phat_576 | chr13.glm_633 | chr13.gen_395 | 13 | 2.22 Mb | GSSS | Rho5 (mito) |
| PF13_0241 | chr13.phat_452 | chr13.glm_494 | chr13.gen_456 | 13 | 1.73 Mb | GASG | Rho4 |
| PF14_0110 | chr14.phat_108 | Not predicted | chr14.gen_705 | 14 | 453 kb | SSSS | Rho6 (?) |
| MAL8P1.16 | chr8.phat_47 | chr8.glm_34 | chr8.gen_290 | 8 | 135 kb | GAST | Rho7 |

TABLE 1b

| *Toxoplasma gondii* consensus ID | Genbank accession | Motif | Rhomboid |
|---|---|---|---|
| Ctoxoqual_3360 | AA531635 | GAST | TgRho1 |

TABLE 2

| Protein | Species | Accession no. |
|---|---|---|
| PfTRAP | *Plasmodium falciparum* | U67764 |
| PfCTRP | *Plasmodium falciparum* | U34363 |
| PfAMA1 | *Plasmodium falciparum* | AF277003 |
| EBL-175 | *Plasmodium falciparum* | AAM33518 |
| MAEBL | *Plasmodium falciparum* | AY042084 |
| TgMIC2 | *Toxoplasma gondii* | TGU62660 |

TABLE 2-continued

| Protein | Species | Accession no. |
|---|---|---|
| TgMIC6 | Toxoplasma gondii | AF110270 |
| TgMIC12 | Toxoplasma gondii | Opitz et al. |
| TgAMA1 | Toxoplasma gondii | AF010264 |
| PbTRAP | Plasmodium berghei | U67763 |

TABLE 2-continued

| Protein | Species | Accession no. |
|---|---|---|
| EtMIC1 | Eimeria tenella | AF032905 |
| EtMIC4 | Eimeria tenella | CAC34726 |
| Sm70 | Sarcocystis muris | AAK35069 |

The invention claimed is:

1. An method for identifying a compound which inhibits infectivity of a protozoan pathogen, which method comprises:
   (a) contacting an isolated Rhomboid polypeptide and an isolated substrate polypeptide in the presence of a test compound; and
   (b) determining proteolytic cleavage of the substrate polypeptide,
   wherein a decrease in cleavage in the presence of the test compound relative to the absence of test compound is indicative that the test compound inhibits infectivity of a protozoan pathogen.

2. A method according to claim 1 wherein the protozoan pathogen is an apicomplexan pathogen.

3. A method according to claim 2 wherein the apicomplexan pathogen is selected from the group consisting of *Plasmodium*, *Toxoplasma*, *Eimeria*, *Sarcocystis*, *Cyclospora*, *Isospora*, *Cryptosporidium*, *Babesia* and *Theileria*.

4. A method according to claim 1 wherein the Rhomboid polypeptide is a protozoan Rhomboid protein.

5. A method according to claim 1 wherein the substrate polypeptide comprises a lumenal domain and a TMD, the TMD having a region proximal to the lumenal domain which comprises one or more of residues 138-144 of the *Drosophila* Spitz sequence (SEQ ID NO:1, ASIASGA).

6. A method according to claim 5 wherein the substrate polypeptide comprises a TMD and a lumenal domain, the TMD having a region proximal to a lumenal domain which has the sequence of residues 138-144 of *Drosophila* Spitz SEQ ID NO:1.

7. A method according to claim 5 wherein the substrate polypeptide is an adhesive micronemal polypeptide.

8. A method according to claim 5 wherein the substrate polypeptide is Ama-1 or CTRP.

9. A method according to any one of the preceding claims wherein the substrate polypeptide and the Rhomboid polypeptide comprise ER (endoplasmic reticulum) retention signals.

10. A method according to claim 8 wherein the endoplasmic reticulum retention signals are (SEQ ID NO:2) KDEL or K K Xaa Xaa.

11. A method according to claim 1 wherein the substrate polypeptide comprises an extracellular domain having a detectable label.

12. A method according to claim 11 wherein the detectable label is GFP.

13. A method according to claim 1 wherein said Rhomboid polypeptide and said substrate polypeptide are expressed in a host cell from heterogeneous nucleic acid.

14. A method according to claim 1 comprising the further steps of;
   (c) bringing into contact an isolated human Rhomboid polypeptide and a polypeptide substrate in the presence of the test compound; and,
   (d) determining proteolytic cleavage of the substrate by the human Rhomboid polypeptide.

15. A method according to claim 1 comprising identifying said test compound as a modulator of adhesive micronemal polypeptide cleavage.

16. A method according to claim 15 further comprising determining the ability of said test compound to inhibit the invasiveness of a protozoan pathogen.

17. A method according to claim 15 comprising isolating said test compound.

18. A method according to claim 17 comprising synthesising the test compound.

19. A method according to claim 17 comprising modifying the test compound to optimise its pharmacological properties.

20. A method according to claim 15 comprising formulating said test compound in a pharmaceutical composition with a pharmaceutically acceptable excipient, vehicle or carrier.

* * * * *

SEQUENCE LISTING

```
<160> NUMBER OF SEQ ID NOS: 13

<210> SEQ ID NO 1
<211> LENGTH: 7
<212> TYPE: PRT
<213> ORGANISM: Drosophila melanogaster

<400> SEQUENCE: 1

Ala Ser Ile Ala Ser Gly Ala
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic motif

<400> SEQUENCE: 2

Lys Asp Glu Leu
1

<210> SEQ ID NO 3
<211> LENGTH: 27
<212> TYPE: PRT
<213> ORGANISM: Eimeria tenella

<400> SEQUENCE: 3

Gly Phe Pro Thr Ala Ala Val Ala Gly Gly Val Gly Gly Val Leu Leu
1               5                   10                  15

Leu Ala Ala Val Gly Gly Gly Val Ala Ala Tyr
            20                  25

<210> SEQ ID NO 4
<211> LENGTH: 26
<212> TYPE: PRT
<213> ORGANISM: Toxoplasma gondii

<400> SEQUENCE: 4

Ser Gly Ile Ala Gly Ala Ile Ala Gly Gly Val Ile Gly Gly Leu Ile
1               5                   10                  15

Leu Leu Gly Ala Ala Gly Gly Ala Ser Tyr
            20                  25

<210> SEQ ID NO 5
<211> LENGTH: 27
<212> TYPE: PRT
<213> ORGANISM: Toxoplasma gondii
```

```
<400> SEQUENCE: 5

Ser Gly His Ala Gly Ala Ile Ala Gly Gly Val Ile Gly Gly Leu Leu
 1               5                  10                  15

Leu Leu Ser Ala Ala Gly Ala Gly Val Ala Tyr
            20                  25

<210> SEQ ID NO 6
<211> LENGTH: 27
<212> TYPE: PRT
<213> ORGANISM: Toxoplasma gondii

<400> SEQUENCE: 6

Gly Val Pro Val Ala Ala Ile Ala Gly Gly Val Val Gly Gly Val Leu
 1               5                  10                  15

Leu Ile Ala Gly Gly Ala Gly Ala Ala Val Tyr
            20                  25

<210> SEQ ID NO 7
<211> LENGTH: 25
<212> TYPE: PRT
<213> ORGANISM: Plasmodium berghei

<400> SEQUENCE: 7

Ser Asn Asn Gly Ile Lys Ile Ala Gly Gly Ile Gly Gly Leu Ala
 1               5                  10                  15

Ile Ile Gly Cys Ile Gly Val Gly Tyr
            20                  25

<210> SEQ ID NO 8
<211> LENGTH: 25
<212> TYPE: PRT
<213> ORGANISM: Plasmodium falciparum

<400> SEQUENCE: 8

Ser Asp Asn Lys Tyr Lys Ile Ala Gly Gly Ile Ala Gly Gly Leu Ala
 1               5                  10                  15

Leu Leu Ala Cys Ala Gly Leu Ala Tyr
            20                  25

<210> SEQ ID NO 9
<211> LENGTH: 26
<212> TYPE: PRT
<213> ORGANISM: Eimeria tenella

<400> SEQUENCE: 9

Gly Phe Pro Thr Ala Ala Val Ala Gly Gly Val Ala Gly Gly Val Leu
 1               5                  10                  15

Ala Ile Ala Ala Gly Ala Gly Ala Phe Tyr
            20                  25

<210> SEQ ID NO 10
<211> LENGTH: 27
<212> TYPE: PRT
<213> ORGANISM: Sarcocystis muris

<400> SEQUENCE: 10

Gly Met Pro Thr Ala Ala Ile Ala Gly Gly Ile Val Gly Gly Val Leu
 1               5                  10                  15

Leu Leu Gly Ala Ala Gly Gly Gly Ala Ala Tyr
            20                  25
```

```
<210> SEQ ID NO 11
<211> LENGTH: 26
<212> TYPE: PRT
<213> ORGANISM: Toxoplasma gondii

<400> SEQUENCE: 11

Gly Ser Asn Thr Ala Leu Ile Ala Gly Leu Ala Val Gly Gly Val Leu
 1               5                  10                  15

Leu Leu Ala Leu Leu Gly Gly Gly Cys Tyr
            20                  25

<210> SEQ ID NO 12
<211> LENGTH: 30
<212> TYPE: PRT
<213> ORGANISM: Drosophila melanogaster

<400> SEQUENCE: 12

Pro Arg Pro Met Leu Glu Lys Ala Ser Ile Ala Ser Gly Ala Met Cys
 1               5                  10                  15

Ala Leu Val Phe Met Leu Phe Val Cys Leu Ala Phe Tyr Leu
            20                  25                  30

<210> SEQ ID NO 13
<211> LENGTH: 30
<212> TYPE: PRT
<213> ORGANISM: Drosophila melanogaster

<400> SEQUENCE: 13

Asn Arg Val Met Leu Glu Lys Ala Ser Ile Val Ser Gly Ala Thr Leu
 1               5                  10                  15

Ala Leu Leu Phe Met Ala Met Cys Cys Val Val Leu Tyr Leu
            20                  25                  30
```